United States Patent [19]

Kronenberg

[11] Patent Number: 4,595,653

[45] Date of Patent: Jun. 17, 1986

[54] PROCESS FOR ASSAYING CELLULAR IMMUNITY

[75] Inventor: Lee H. Kronenberg, San Diego, Calif.

[73] Assignee: Lee BioMolecular Research Laboratories, Inc., San Diego, Calif.

[21] Appl. No.: 709,062

[22] Filed: Mar. 6, 1985

Related U.S. Application Data

[62] Division of Ser. No. 269,557, Jun. 9, 1981, Pat. No. 4,568,542.

[51] Int. Cl.$^4$ .............................................. C12Q 1/70
[52] U.S. Cl. ............................................ 435/5; 435/6
[58] Field of Search ......................................... 435/5, 6

[56] References Cited

PUBLICATIONS

Hyde, J. et al., *Biochem.* 17, 1251 (1978).
Isaacs, S. et al., *Biochem.* 16, 1058 (1977).
Musajo, L. et al., *Experentia* 21, 22 (1965).
Musajo, L. et al., *Photochem. Photobiol.* 6, 711 (1967).
Musajo, L. et al., *Photochem. Photobiol.* 6, 927 (1967).
Nakashima, K. et al., *J. Bio. Chem.* 253, 8680, (1978).
Cole, R. S., *Biochim. Biophys. Acta.* 217, 30 (1979).
Colombo, G. et al., *Prog. Biochem. Pharmacol.* 1, 392, (1965).
Hallick, L. et al., *J. Virol.* 27, 127, (1978).
Hanson, C. et al., *J. Gen. Virol.* 40, 345 (1978).
Hearst, J. et al., *Nucleic Acids Res.* 4, 1339, (1977).
Hochkeppel, H-K, et al., *Biochem.* 18, 2905, (1979).
Nakashima, K. et al., *J. Virol.* 32, 838, (1979).
Scott, B. et al., *Mut. Res.* 39, 29 (1976).
Shen, C-K, et al., *Proc. Nat. Acad. Sci. USA* 73, 2649, (1976).
Shen, C-K, et al., *J. Mol. Biol.* 116, 661, (1977).
Song, P-S, et al., *Photochem. Photobiol.* 29, 1177 (1979).
Chem. Abstracts 93, 142760s.
Chem. Abstracts 88, 182868m.

*Primary Examiner*—Sam Rosen
*Attorney, Agent, or Firm*—Robbins & Laramie

[57] ABSTRACT

The present invention describes the inactivation of target cells by treatment of said cells with psoralens and irradiation with long wave length ultraviolet light. The inactivated cells are shown to be antigenic and are shown to be non-infective. These cells are useful as target antigens for in vitro assays of cellular immunity. Diagnostic kits containing the inactivated, target cells are prepared for use in serologic assays. Since the inactivated cells are immunogenic and non-infective, they are also useful as vaccines.

14 Claims, 4 Drawing Figures

PROCESS FOR ASSAYING CELLULAR IMMUNITY

This application is a division of application Ser. No. 269,557, filed June 9, 1981 now U.S. Pat. No. 4,568,542.

BACKGROUND OF THE INVENTION

Psoralen and psoralen derivatives are polycyclic planar molecules which posses an affinity for nucleic acids, both deoxyribo- and ribo-nucleic acids. See Song, P-S and Tapley, K. J., *Photochem Photobiol* 29, 1177 (1979) and Scott, B. R., et al., *Mutation Research* 39, 29 (1976). The structure of psoralen is

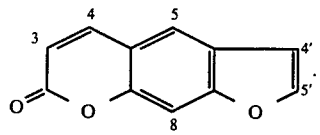

Specific psoralen derivatives include, among others, 8-methoxpsoralen, 4,5',8-trimethylpsoralen(trioxsalen), 4'-methoxymethyl-4,5',8-trimethylpsoralen, 4'-aminomethyl-4,5',8-trimethylpsoralen (AMT) and 4'-hydroxymethyl-4,5',8-trimethylpsoralen (HMT). As used hereinafter, psoralen or psoralens will be used to refer to both psoralen and psoralen derivatives unless indicated otherwise.

Psoralen is added covalently to a pyrimidine base by a photochemical reaction when a psoralen-nucleic acid complex is irradiated by long wave length ultraviolet light (LWUV). Cole, R. S., *Biochim, Biophys Acta* 217, 30 (1970) and Musajo, L., et al., *Photochem Photobiol* 6, 711 (1967). LWUV is ultraviolet light generally having a wavelength of 320–380 nm. Hanson, C. V., et al., *J. Gen. Virol.* 40, 345 (1978), Hearst, J. E. and Thiry, L., *Nucleic Acids Research* 4, 1339 (1977) and Musago, L., et al., *Experientia* 21, 22 (1965) have shown that DNA viruses and RNA viruses are inactivated, i.e. they have lost their ability to infect, by treating the viruses with psoralens and irradiation with LWUV. It has been found that AMT and HMT are the most effective. Hanson et al., also set forth at pages 346–7 numerous advantages of psoralens which include their ability to readily pass through cellular and nuclear membranes and their non-reactivity in the absence of irradiation with LWUV. At page 345, Hanson et al., have further suggested that they would not expect treatment of viruses with psoralens and irradiation with LWUV to cause modification of surface antigens. Thus, they expect the viruses to maintain their antigenicity.

Although psoralens have been utilized for treating viruses, the effects of psoralens on virus-infected cells has not been studied. It was not known whether psoralens would inactivate virus-infected cells so that they would lose their infectivity. It was also not known how psoralen treatment would affect the antigenicity of the virus-infected cells. If psoralen treatment would inactivate virus-infected cells but would not affect their antigenicity, these cells could then be useful for in vitro assays of cellular immunity.

In the past, in vitro assays of virus-specific cellular immunity generally involved the exposure of viable effector lymphocytes to viral antigens, followed by the measurement of some presumably relevant cellular response, such as proliferation, lymphokine release, or cytotoxicity. See Shillitoe, E. J. and Rapp, R., *Springer Sem. Immunopathol* 2, 237 (1979) and Sissons, J. G. P. and Oldstone, M. B. A., *J. Infect. Dis.* 142, 114 (1980). Because virus infection of the effector lymphocytes may alter these measured responses, the virus antigens employed should be noninfectious. Plaeger-Marshall, S. and Smith J. W., *J. Inf. Dis.* 138, 506 (1978); Rosenberg, G. L., et al., *Proc. Nat. Acad Sci USA* 69, 756 (1972); and, Russell, A. S., *Am. J. Clin. Path.* 60, 826 (1973). Moreover, since in vivo cell-mediated immunity to many viruses, especially to members of the Herpes virus group, may involve the interaction of effector lymphocytes with virus-infected cells rather than with cell-free virus or soluble antigens (Notkins, A. L., *J. Cell Immunol.*, 11, 478 (1974)), it may be important to use antigen-bearing virus-infected cells rather than cell-free virus or soluble virus antigens in in vitro assays of cellular immunity. Thus, inactivated, virus-infected cells having antigenicity but no infectivity would be useful in these circumstances. The present invention describes the inactivation of virus-infected cells by treatment of these cells with psoralens and irradiation with LWUV. These inactivated, virus-infected cells were found to be antigenic and not infective. These cells are useful for in vitro assays of cellular immunity and as target antigens in serologic assays. Diagnostic kits containing the inactivated cells are prepared for such uses.

Inactivation of target cells with psoralen and irradiation with LWUV have the following advantages; it eliminates the infectivity of the cells in a much shorter time, requires low amounts of radiant energy, permits the recovery of essentially all of the cells initially present and preserves native antigenicity by all criteria examined.

SUMMARY OF THE INVENTION

Target cells are treated with psoralens and irradiation with LWUV in order to inactivate them. Target cells refer to normal cells as well as virus-infected cells. Inactivated target cells refer to cells in which the nucleic acids have been inactivated. The inactivated target cells, however, remain antigenic. Inactivated, virus-infected cells refer to virus-infected cells which are no longer able to release viral particles, sub-viral components or viral nucleic acids which are infective, i.e., they are no longer infective. This treatment results in the loss of infectivity of the cells without the loss of the cells' antigenic properties. As a result, these inactivated cells remain able to stimulate virus-specific lymphocyte proliferation. Because of this ability, the inactivated cells are useful as target antigens for in vitro assays of cellular immunity and can be packaged in diagnostic kits. The inactivated cells are also useful as vaccines.

DETAILED DESCRIPTION OF THE INVENTION

Figure 1:
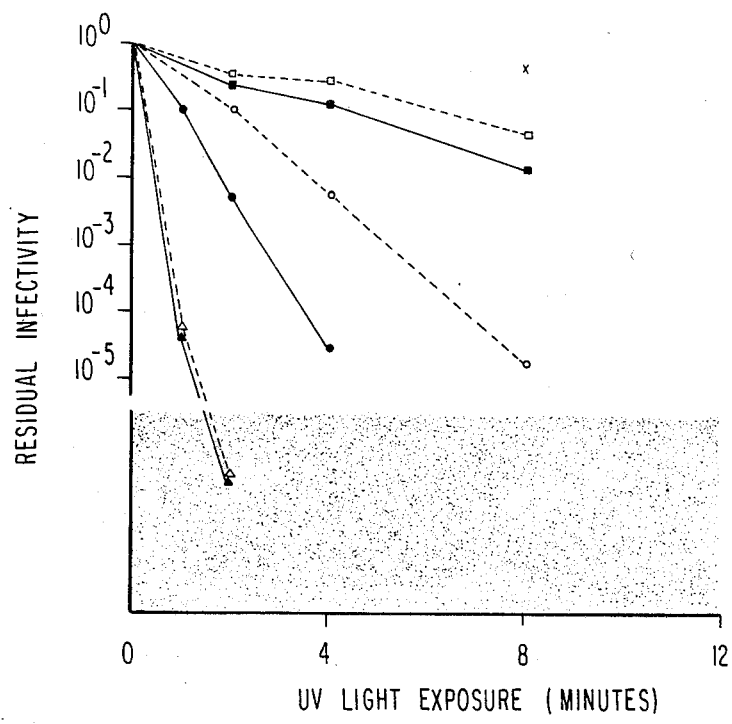
FIG. 1 illustrates the inactivation of cell-free HSV.

Target cells are inactivated by treatment with psoralens and irradiation with LWUV. Target cells refer to normal cells or virus-infective cells which possess cell-associated antigens capable of stimulating sensitized lymphocytes to proliferate or to display cytotoxicity against the target cells. Normal cells refer to all cells which are not virus-infected, e.g., nerve cells and tumor cells. Target cells are prepared in any conventional manner, such as isolation from a suitable source, man, animal or tissue culture containing them. For example, nerve or muscle cells can be isolated from human nerve or muscle tissue, respectively, and tumor cells can be isolated from patients having cancer. Virus-infected cells may also be prepared in vitro. This is accomplished by infecting a culture of a desired cell type with a desired virus. For example, rabbit kidney (RK13) cells are infected with Herpes simplex virus (HSV) by incubating a confluent monolayer culture of RK13 cells and HSV for 24 hours. At this time 90% of the cells show cytopathic effects. These cells are then isolated and stored for further usage. In a similar manner, other types of cells can be infected by any virus which is capable of infecting a particular type of cell. Viruses which infect cells include, but are not limited to, HSV, varicella, cytomegalovirus and influenza. It is preferable to prepare virus-infected cells in vitro so that infected cells having a specific virus are prepared.

The target cells are inactivated by treating them with psoralen and irradiation with LWUV. This is accomplished by adding a solution of psoralen to the target cells and then irradiating the resulting mixture with LWUV. The desired psoralen is dissolved in a suitable solvent, for example, ethanol or dimethyl sulfoxide (DMSO). When ethanol is the solvent, the ethanol is partially evaporated off of an aliquot of the psoralen solution containing the appropriate amount of the desired psoralen so that the final ethanol concentration in the cell and psoralen mixture is no more than 2%. When DMSO is the solvent, the desired psoralen is usually dissolved in 100% DMSO and working solutions prepared from this by diluting with sterile distilled water. A working solution is then added to the target cells such that the final DMSO concentration is less than 1%.

The final concentration of psoralen in the psoralen/target cells mixture is 0.1–250 $\mu$g/ml. The amount of psoralen utilized is generally dictated by the specific psoralen compound selected and the period of time for the irradiation with LWUV. The amount of any specific psoralen compound required to eliminate infectivity of virus-infected cells, for example, is readily determined by treating the cells with various concentrations of the specific compounds, irradiating with LWUV for various lengths of time and measuring the infectivity. The amount of any specific psoralen required to inactivate normal cells is similarly determined except that the ability of cell division is measured. Although any psoralen compound can be utilized, it is preferred that AMT and HMT be utilized. These compounds are preferred because they are highly effective at low concentrations and short irradiation times. For example, a concentration of 10 $\mu$g/ml of either HMT or AMT is able to eliminate measurable infectivity of virus-infected cells after 4 minutes of irradiation for HSV and 16 minutes for irradiation for influenza virus. The final concentration of cells in the psoralen/target cells mixture is $10^3$–$10^9$ cells/ml.

Irradiation of the psoralen/target cells mixture is performed utilizing a light source which emits ultraviolet light having a wavelength within the range of 320–380 nm, i.e., LWUV. One suitable light source is a 15W General Electric (F15 T8) black light which emits 90% of its radiant energy between 355–380 nm. The mixture is placed in a suitable receptacle, such as a petri dish, within wells of a tissue culture dish or pumped through a continuous flow cell, and placed parallel to the light source for the appropriate length of time. Suitable lengths of time which can be determined as described above are 0.1–100 minutes. The receptacle is positioned parallel to the light source such that energy output measured within the receptacle is 100–100,000 ergs/sec/cm$^2$.

Virus-infected cells are inactivated by the psoralen-LWUV treatment described above. These cells have lost their infectivity as measured in a virus plaque assay. This treatment, however, does not affect the antigenicity of the virus-infected cells. The treated cells have the same antigenic properties as do virus-infected cells which have not undergone this treatment, i.e., untreated cells; as determined by an immunofluorescent assay and an [$^{125}$I] staphylococcal protein A (SPA) radioimmunoassay. Since the inactivated, virus-infected cells have not lost their antigenicity, they react with antibodies and consequently are useful as target antigens in conventional immunoassays. One method of assaying for antibodies to membrane antigens using virus-infected cells is described by Zaia, J. A., and Oxman, M. N., *J.Infect.Dis.*, 136, 519 (1977). Furthermore, this inactivation procedure does not alter the virus-infected cells' ability to stimulate cellular immunity as determined by a lymphocyte proliferation assay. Normal cells are also inactivated by the psoralen-LWUV treatment described above. This treatment does not affect the antigenicity of the normal cells as determined by the immunofluorescent and [$^{125}$I] SPA assays. Thus, they can be utilized for in vitro diagnosis of auto-immune diseases, such as rheumatoid arthritis or self-demylenating diseases. In addition, inactivated tumor cells can be utilized to determine if a cancer patient has a defect in his cellular immunity or also to determine the extent of cellular immunity against the tumor of origin. Consequently, the inactivated, target cell are useful as target antigens in in vitro assays of cellular immunity.

Cellular immunity is assayed in vitro by several methods. See Shillitoe and Rapp, supra, and Sissons and Oldstone, supra. These methods include a lymphocyte proliferation assay and a cytotoxicity assay. Generally in the lymphocyte proliferation assay, donor lymphocytes are incubated in culture with a mitogen or an antigen, e.g., the inactivated virus-infected cells, in a medium containing [$^3$H] thymidine. After a sufficient length of time has elapsed, the lymphocytes are collected and the amount of [$^3$H] thymidine incorporation is measured. See also Bellanti, J. A., et al, *Manual of Clin.Immunol.*, Ed. Rose, N. R., and Friedman, J., p. 155–165, Am. Soc. Microbiol., Washington, D.C. 1976. If the donor is immune to the viral antigen, the inactivated virus-infected cells will stimulate lymphocyte proliferation. Similarly, if the donor suffers from an auto-immune disease, the appropriate inactivated normal cells will stimulate lymphocyte proliferation. For example, inactivated muscle cells containing acetylcholine receptors will stimulate lymphocyte proliferation in a person suffering from muscular dystrophy. Also, inactivated nerve cells, for example, neuroblastoma or glial cells, will stimulate lymphocyte proliferation in patients suffering from multiple sclerosis and other auto-immune diseases of nerve cells. In the cytotoxicity assay, the target cell, e.g., the inactivated, virus-infected cells are labelled. Although any radiolabel may be used, it is preferred to utilize $^{51}$Cr since it fulfills the criteria of cytotoxicity assays. (See Sissons and Oldstone, supra.) The virus-infected cells are labelled by the procedure as described in Bellanti, J. A., et al, supra. The labelled, virus-infected cells are incubated with donor lymphocytes for a sufficient period of time. The amount of $^{51}$Cr released into the supernatant as a result of cytolysis is measured. If the donor is immune to the viral antigen, a portion of the lymphocytes will be cytoxic for that antigen. These lymphocytes will cause the lysis of the inactivated, virus-infected cells. Thus, use of the inactivated, virus-infected cells will distinguish between immunized and non-immunized donors in either of these two assays. Similarly, lymphocytes from a donor having an auto-immune disease will cause the lysis of the labelled, inactivated normal cells relating to that disease, e.g., as discussed above for muscle cells and muscular dystrophy and the others. Use of the inactivated normal cells will assist in the diagnosis of auto-immune diseases. Diagnostic kits are prepared such that they contain either inactivated target cells or radiolabelled, inactivated target cells. These diagnostic kits are utilized for assaying cellular immunity as described above.

The inactivated target cells retain their normal antigenic determinants and are able to elicit a cellular immunity response. Thus, the inactivated target cells can be utilized as a vaccine. For example, a preparation of inactivated, virus-infected cells can be used as a vaccine against the virus. Such a vaccine may provide better protection than a simple viral vaccine since the cellular immunity response may be directed towards virus-infected cells. This is advantageous since infected cells also contain major histocompatibility and other immune response antigens on their surfaces which are not on the surface of viruses used as vaccines. These other antigens are often required for full expression of immunity. Similarly, inactivated tumor cells can be administered to the patient from which the original cells were obtained in order to provide a tumor vaccine containing inactivated autologous tumor cells.

The details of the present invention will be further described by the following specific, non-limiting examples. Rabbit kidney (RK13) cells were obtained from Drs. Charles Scott and Stewart Sell, University of California, San Diego. Madin Darby canine kidney (MDCK) cells and influenza A/Hong Kong/68 (H3N2) virus were obtained from Drs. Brian Murphy and Robert Chanock, National Institutes of Health, Bethesda, Md. The culture media were obtained from Grand Island Biological Company, Grand Island, N.Y. The MacIntyre strain of HSV type I (No. VR-539) was obtained from the American Type Culture Collection, Rockville, Md. AMT and HMT were obtained from Calbiochem-Behring, La Jolla, Calif. Fluorescein conjugated rabbit anti-serum to HSV type I fluorescein conjugated goat anti-rabbit globulin were obtained from M. A. Byproducts, Bethesda, Md. TPCK-trypsin and trypsin were purchased from Worthington Biochemicals, Freehold, N.J. and Difco, Detroit, Mich. respectively.

In the Examples which follow, cells were grown in 150 cm$^2$ plastic cell culture bottles (Costar, Microbiological Association, Bethesda, Md.) in an atmosphere of 5% CO$_2$ in air at 37° C., using Dulbecco modified Eagle medium plus 100 U/ml penicillin and 100 U/ml streptomycin (DMEM) supplemented with 10% fetal bovine serum (FBS) for the RK13 cells and with 5% FBS for the MDCK cells. A strain of diploid human fibroblasts (350 Q) initiated from newborn foreskin at the Virus Research Unit, Children's Hospital, Boston, Mass. was used between passages 18 and 30. The 350 Q cells were grown in the same manner as the RK13 cells.

EXAMPLE 1

Preparation of Cell Free Virus and Virus-Infected Cells (a) HSV. Confluent monolayer cultures of RK13 cells were infected with HSV at a multiplicity of infection (MOI) of 1 plaque forming unit (PFU) per cell and incubated at 36° C. in DMEM plus 2%. At 24 hours postinfection, when more than 90% of the cells showed cytopathic effects, the culture medium was harvested and clarified by centrifugation at 800×g for 10 minutes. This clarified medium, which contained $9 \times 10^5$ PFU/ml of cell-free HSV, was stored in aliquots at −70° C. The infected cells remaining in the monolayer were rinsed with Puck's saline A (Puck, T. T. et al., J. Exp. Med. 106, 145 (1957) and dispersed with 5 ml of 0.05% trypsin—0.02% EDTA at 35° C. When the cells were detached, 1 ml of FBS was added and cell aggregates were dispersed by gentle pipetting. The cells were then pelleted by centrifugation at 400×g for 10 minutes, resuspended at $2.0 \times 10^6$ cells/ml in DMEM containing 8% dimethylsulfoxide (DMSO) and 30% FBS, and frozen in aliquots at −70° C.

(b) Influenza Virus. Confluent monolayer cultures of MDCK cells were infected with influenza virus at an MOI of 0.04 PFU per cell and incubated at 37° C. in DMEM containing 0.5 μg/ml TPCK trypsin. At 48 hours postinfection, when more than 90% of the cells showed cytopathic effects, the medium was harvested, clarified by centrifugation and stored in aliquots at −70° C. The titer of cell-free influenza virus was $1.2 \times 10^8$ PFU/ml. The infected cells remaining in the monolayer were dispersed with 0.5% trypsin-0.2% EDTA, pelleted, resuspended at $2.8 \times 10^7$ cells/ml in DMEM plus 8% DMSO and 30% FBS, and frozen in aliquots at −70° C.

EXAMPLE 2

Virus Plaque Assays (a) HSV. Ten-fold serial dilutions of cell-free virus or virus-infected cells, treated or untreated, were inoculated onto monolayer cultures of 350 Q cells in 6-well plastic cell culture dishes (Costar). After a one hour adsorption at room temperature, the cultures were overlayed with Eagle basal medium containing 0.5% agarose, 100 U/ml penicillin and 100 μg/ml streptomycin. They were incubated in a humidified atmosphere of 5% CO$_2$ in air at 35° C. for 3 days. Plaques were counted using an inverted microscope at 40×magnification.

(b) Influenza virus. Ten-fold serial dilutions of cell-free virus or virus-infected cells treated or untreated, were inoculated onto monolayer cultures of MDCK cells in 6-well plastic cell culture dishes (Costar). After a one hour adsorption at room temperature, the cultures were overlayed with Liebowitz 15 medium containing 0.9% agarose, 100 U/ml penicillin, 100 μg/ml streptomycin and 0.5 μg/ml TPCK trypsin. They were incubated in air at 35° C. for 3 days. Plaques were counted directly without staining.

EXAMPLE 3

Psoralen-LWUV Inactivation of Cell Free Virus and Virus-Infected Cells

Stock solutions containing 1 mg/ml of AMT or HMT were prepared in DMSO and stored at −20° C. The concentrations were confirmed spectrophotometrically. (Isaacs, S. T., et al., *Biochemistry* 16, 1058 (1977).) Working solutions containing 10× the desired final concentration of psoralen were prepared in sterile distilled water. The final concentration of DMSO was always <1%. Psoralen solutions were always protected against exposure to light. The final concentration of AMT or HMT used was 0.1 or 1.0 or 10 μg/ml.

Figure 2:
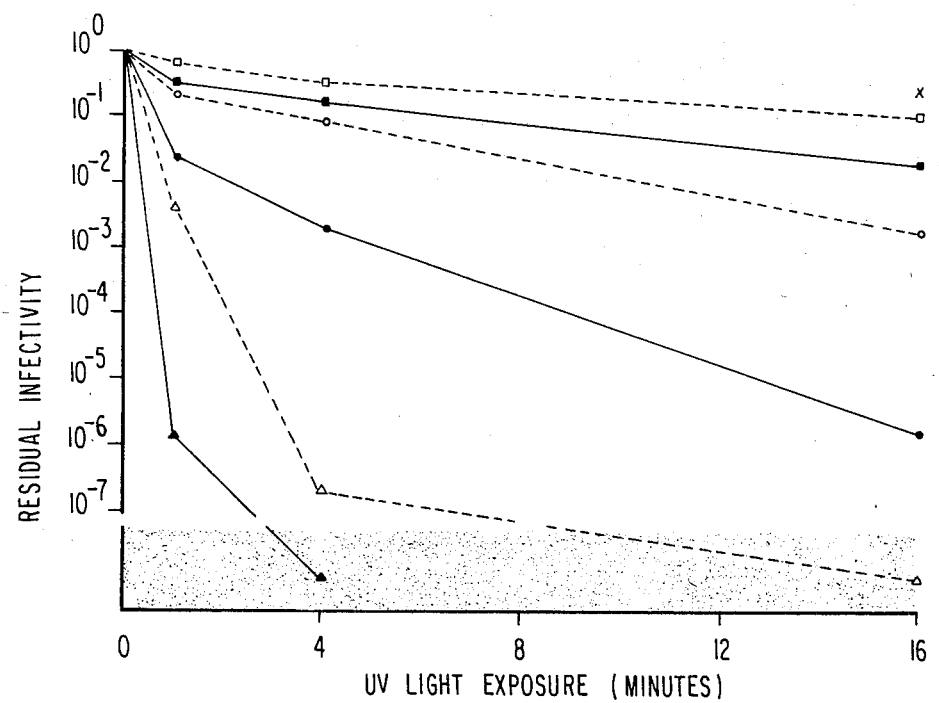
FIG. 2 illustrates the inactivation of cell-free influenza virus.
Figure 3:
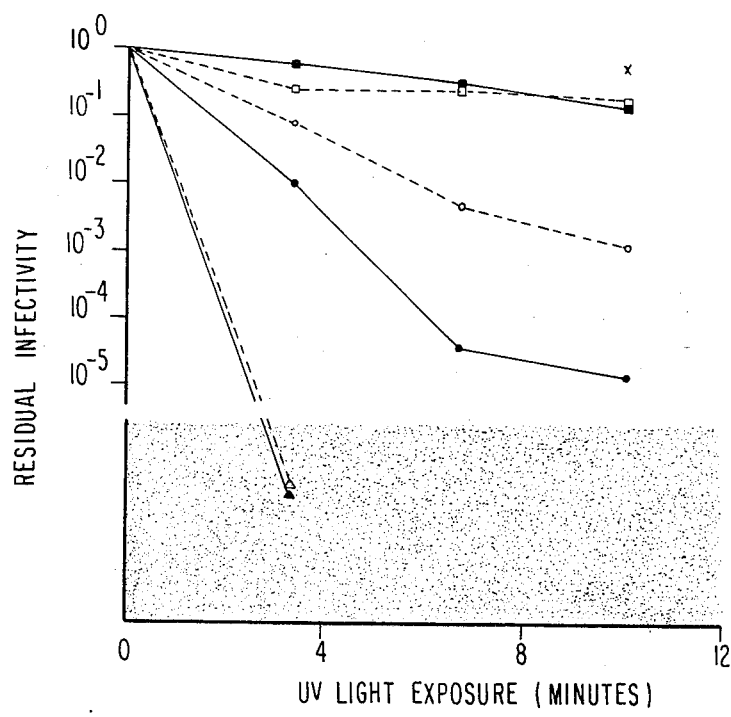
FIG. 3 illustrates the inactivation of HSV-infected RK13 cells.
Figure 4:
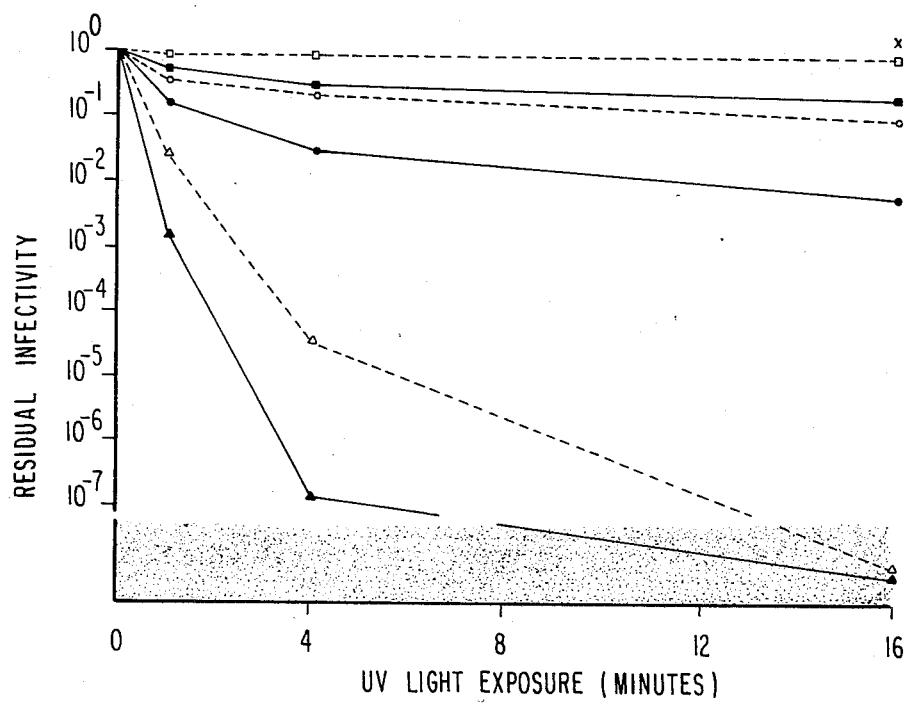
FIG. 4 illustrates the inactivation of influenza virus-infected MDCK cells.

Just prior to irradiation, one part of a 10× solution of psoralen was mixed with 9 parts of DMEM plus 2% FBS containing cell-free virus or virus-infected cells ($2.2 \times 10^6$ cells/ml). One ml of this mixture was placed in a 1.6 cm diameter well of a 24-well flat bottomed tissue culture dish (Costar). The bottom of the well was held directly over the LWUV source and the plate was agitated manually to ensure mixing and uniform exposure. The LWUV light source was a horizontally mounted 15W General Electric (F15 T8) black light which emitted 90% of its radiant energy between 355 and 380 nm. The energy output was $1.2 \times 10^4$ ergs/sec/cm$^2$ when measured within the wells of a 24-well flat bottomed tissue culture dish (Costar) held directly over the light source. The cell-free virus and virus-infected cells were exposed to the LWUV for varying periods of time. In all four instances, the rate of inactivation as determined by virus plaque assays was proportional both to psoralen concentration and to total LWUV dose. See FIGS. 1-4 for inactivation of (1) cell-free HSV, (2) cell-free influenza virus, (3) HSV-infected RK13 cells and (4) influenza virus-infected MDCK cells respectively. In each figure, the boxes, circles and triangles represent 0.1 μg/ml, 1.0 μg/ml and 10.0 μg/ml respectively. The open symbols refer to HMT and the closed symbols refer to AMT. The titer of virus exposed to LWUV in the absence of AMT or HMT is indicated by the symbol X. The shaded area indicates the lower limit of measurable infectivity.

At equivalent psoralen concentrations the rate of inactivation of both cell-free viruses was greater with AMT than with HMT. A $10^4$-fold reduction of HSV infectivity required $6.5 \times 10^5$ ergs/cm$^2$ of LWUV (0.9 minutes of LWUV exposure) in the presence of 10 μg/ml of either psoralen. A $10^4$-fold reduction of influenza virus infectivity required $5.0 \times 10^5$ ergs/cm$^2$ of LWUV (0.7 minutes of LWUV exposure) in the presence of 10 μg/ml of AMT. The infectivity of virus-infected cells was, in general, more rapidly abolished in the presence of AMT than in the presence of the same concentration of HMT. A $10^4$ fold reduction in the infectivity of HSV-infected cells required $1.4 \times 10^6$ ergs/cm$^2$ of LWUV (2 minutes of LWUV exposure) in the presence of 10 μg/ml of either psoralen. A $10^4$ fold reduction in the infectivity of influenza virus-infected cells also required $1.4 \times 10^6$ ergs/cm$^2$ of LWUV (two minutes of LWUV exposure) in the presence of 10 μg/ml of AMT. Recovery of intact virus-infected cells following all tested periods of exposure to LWUV in the presence of either psoralen was always greater than 90% of the cells initially present.

EXAMPLE 3

Antigenicity of Virus-Infected Cells (a) Preparation of Antisera. Rabbit antiserum to influenza A/Hong Kong/68 (H3N2) was prepared in New Zealand White (NZW) rabbits immunized by subcutaneous (SC) inoculation of $10^9$ PFU of egg-grown virus (purified in a 10–40% potassium tartrate density gradient) in 1 ml of complete Freund's adjuvant, followed by two SC booster injections of $10^9$ PFU of virus without adjuvant. Serum was prepared from blood obtained by cardiac puncture 4 weeks after the second injection. The antiserum had a hemagglutination-inhibition titer of 512 against the immunizing virus. Rabbit antiserum to HSV was prepared in NZW rabbits immunized by three monthly intramuscular inoculations of approximately $10^{5.5}$ PFU of virus. Serum was prepared from blood drawn by cardiac puncture 1 week after the last inoculation. This antiserum had a complement fixation titer of 1024 against the immunizing virus.

(b) Immunofluorescent Staining of Virus-Infected Cells. HSV-infected cells were stained by the direct fluorescent antibody technique using fluorescein conjugated rabbit antiserum to HSV type I. $10^5$ cells were suspended in 0.025 ml of the conjugated antiserum diluted 1:10 in phosphate buffered saline (PBS) in wells of plastic U-plates (Cooke Laboratory Products, Alexandria, Va.) and incubated at room temperature. After 30 minutes, 0.15 ml of PBS was added to each well and the plates were centrifuged at 400×g for 10 minutes. The supernatant was carefully removed by aspiration and the cells were washed twice with 0.15 PBS per well. Washed pelleted cells were resuspended in 0.020 ml of buffered glycerol (90% glycerol-10% PBS, pH 8.5) and 0.010 ml was placed under a glass coverslip for fluorescent microscopy.

Influenza virus-infected cells were stained by the indirect fluorescent antibody technique using rabbit antiserum to influenza virus and fluorescein conjugated goat anti-rabbit globulin. $10^5$ cells were incubated with rabbit antiserum to influenza virus diluted 1:100 in PBS and then washed three times as above. The washed, pelleted cells were then resuspended in 0.025 ml of fluorescein conjugated goat anti-rabbit globulin diluted 1:10 in PBS and incubated for 30 minutes. The cells were then washed three times with PBS, resuspended in 0.020 ml buffered glycerol, and 0.010 ml placed under a glass coverslip for fluorescent microscopy. In each instance, the cells were examined at a magnification of 400× with a Zeiss Photomicroscope II equipped for epifluorescence. Control (uninfected) cells were included in each assay and all samples were coded prior to examination. Only isolated intact cells were counted, and at least 100 consecutive cells were evaluated for each sample. Membrane fluorescence appeared as a bright rim at the periphery of the infected cells. Uninfected control cells never exhibited discernible fluorescence.

Both HSV and influenza virus-infected cells exhibited membrane fluorescnce which appeared as a bright rim at the periphery of the cells. Psoralen-LWUV inactivation did not result in any discernible reduction in the percentage of cells positive for viral antigens, or in the intensity or morphology of fluorescent staining (Tables 1 and 2). This was true even with conditions of inactivation that eliminated all measurable infectivity. In each Table, the values represent the percent of cells exhibiting membrane fluorescence after immunofluorescent staining. There was no discernible reduction in the intensity of fluorescent staining in any of the irradiated cells. This experiment showed that the inactivated virus infected cells are still antigenic.

TABLE 1

THE EFFECT OF PSORALEN LWUV TREATMENT ON THE ANTIGENICITY OF HSV-INFECTED CELLS.

| | Percent of cells with virus antigen after indicated period of LWUV exposure | | | |
|---|---|---|---|---|
| Psoralen | 0 min | 3.3 min | 6.7 min | 10 min |
| None | 91 | — | — | 92 |
| HMT (0.1 ug/ml) | — | 95 | 93 | 89 |
| HMT (1.0 ug/ml) | — | 85 | 93 | 91 |
| HMT (10 ug/ml) | 95 | 94 | 85 | 91 |
| AMT (0.1 ug/ml) | — | 94 | 87 | 86 |
| AMT (1.0 ug/ml) | — | 88 | 93 | 86 |
| AMT (10 ug/ml) | 87 | 90 | 92 | 88 |

TABLE 2

THE EFFECT OF PSORALEN LWUV TREATMENT ON THE ANTIGENICITY OF INFLUENZA VIRUS-INFECTED CELLS.

| | Percent of cells with virus antigen after indicated period of LWUV exposure | | | |
|---|---|---|---|---|
| Psoralen | 0 min | 1 min | 4 min | 16 min |
| None | 87 | — | — | 88 |
| HMT (0.1 ug/ml) | — | 91 | 80 | 79 |
| HMT (1.0 ug/ml) | — | 94 | 83 | 91 |
| HMT (10 ug/ml) | 85 | 89 | 84 | 84 |
| AMT (0.1 ug/ml) | — | 81 | 90 | 78 |
| AMT (1.0 ug/ml) | — | 88 | 84 | 84 |
| AMT (10 ug/ml) | 87 | 92 | 84 | 84 | the wells of the immunofiltration device for 30 minutes at 37° C. The cells were then washed three times to remove unbound antibody and incubated with 25,000 or 50,000 CPM of [$^{125}$I]SPA per well for 60 minutes at 35° C. The cells were again washed three times to remove unbound [$^{125}$I]SPA, and the bound [$^{125}$I]SPA was measured with a Searle Model 1195 Automatic Gamma Counter.

Influenza antigens on 12,500 infected cells were measured similarly, using a 1:1000 dilution of rabbit antiserum against influenza A/Hong Kong/68 (H3N2) and 50,000 CPM of [$^{125}$I]SPA.

Under the conditions employed herein, the amount of [$^{125}$I]SPA bound in the presence of a constant amount of antiviral antibody is directly proportional to the amount of virus antigen present. Following incubation with viral antibody and then with [$^{125}$I]SPA, equivalent amounts of [$^{125}$I]SPA were bound psoralen-LWUV treated virus-infected cells and the untreated virus-infected cells. There was no reduction in the antigenicity detectable by this method, even in cells which had been rendered completely noninfectious (Tables 3 and 4). In each Table, the values represent the virus-specific CPM. Virus-specific CPM was defined as the CPM bound to cells incubated with anti-serum minus the CPM bound to the same number of cells incubated with control serum. The CPM bound to infected cells incubated with control serum (background CPM) was never more than 10–15% of the CPM bound to infected cells incubated with antiserum. The reported values represent the mean ±SD of four replicates. This experiment further demonstrated that the inactivated, virus-infected cells are antigenic.

TABLE 3

THE EFFECT OF PSORALEN LWUV TREATMENT ON THE ANTIGENICITY OF HSV-INFECTED CELLS

| | Virus-specific CPM of [$^{125}$I] SPA bound to cells exposed to LWUV for the indicated period of time | | | |
|---|---|---|---|---|
| Psoralen | 0 min | 3.3 min | 6.7 min | 10 min |
| None | 1441 ± 42 | — | — | 1498 ± 112 |
| HMT (0.1 ug/ml) | — | 1666 ± 85 | 1478 ± 67 | 1542 ± 137 |
| HMT (1.0 ug/ml) | — | 1553 ± 290 | 1213 ± 70 | 1106 ± 49 |
| HMT (10 ug/ml) | 1131 ± 195 | 1351 ± 23 | 1195 ± 87 | 1427 ± 79 |
| AMT (0.1 ug/ml) | — | 1399 ± 179 | 1382 ± 214 | 1277 ± 81 |
| AMT (1.0 ug/ml) | — | 1472 ± 202 | 1466 ± 257 | 1260 ± 82 |
| AMT (10 ug/ml) | 1138 ± 119 | 1247 ± 116 | 1228 ± 135 | 1217 ± 133 |

TABLE 4

THE EFFECT OF PSORALEN LWUV TREATMENT ON THE ANTIGENICITY OF INFLUENZA VIRUS-INFECTED CELLS.

| | Virus-specific SPA of [$^{125}$I] SPA bound to cells exposed to LWUV for the indicated period of time | | | |
|---|---|---|---|---|
| Psoralen | 0 min | 1 min | 4 min | 16 min |
| None | 2915 ± 441 | — | — | 3192 ± 515 |
| HMT (0.1 ug/ml) | — | 2286 ± 123 | 2736 ± 147 | 2639 ± 503 |
| HMT (1.0 ug/ml) | — | 2461 ± 425 | 3015 ± 282 | 2909 ± 272 |
| HMT (10 ug/ml) | 3629 ± 368 | 2873 ± 197 | 2514 ± 839 | 2670 ± 274 |
| AMT (0.1 ug/ml) | — | 3151 ± 346 | 3248 ± 242 | 2648 ± 156 |
| AMT (1.0 ug/ml) | — | 2346 ± 795 | 3828 ± 337 | 3183 ± 207 |
| AMT (10 ug/ml) | 3018 ± 582 | 3665 ± 510 | 3215 ± 157 | 3056 ± 270 |

(c) [$^{125}$I] Staphylococcal Protein A (SPA) Radioimmunoassay. HSV antigens in HSV-infected cells were measured by means of a [$^{125}$I]SPA immunofiltration assay as described in Cleveland, P. H., et al., *J. Immunol. Meth.* 29, 369 (1979). Briefly, 12,500 or 25,000 cells were incubated with a 1:4000 dilution of rabbit antiserum to HSV type I (or of control rabbit serum) in

EXAMPLE 5

In Vitro Cellular Immunity Assays (a) Lymphocyte Proliferation Assay. Lymphocytes were prepared from defibrinated rabbit blood (Coulson, A. S. and Chalmers, D. G., *Lancet* 1:468 (1964)) or heparinized human blood (Boyum, A., *Scand. J. Clin. Lab. Invest.* 21 (Supp. 97) 51 (1968)) as described herein. Lymphocytes were washed twice in PSA and then suspended at a concentration of $2 \times 10^6$ cells/ml in RPMI 1640 medium supplemented with 100 U/ml penicillin, 100 μg/ml streptomycin, and either 5% heat inactivated (56° C. for 30 minutes) pooled normal rabbit serum or 10% heat inactivated pooled human AB-positive serum (both serum pools prepared in this laboratory). $2 \times 10^5$ lymphocytes in 0.10 ml were dispensed into wells of 96-well flat bottom plastic tissue culture dishes together with 0.05 ml/well RPMI 1640 medium containing the various mitogens or antigens. The lymphocyte cultures were incubated for 5 days at 35° C. in a humidified atmosphere of 5% $CO_2$ in air and 0.25 μCi of [$^3$H]thymidine (New England Nuclear, Boston, MA) in 0.01 ml RPMI 1640 was added to each well at the beginning of the last 24 hours. The lymphocytes were then harvested onto glass fiber filters using an automatic harvester (Titertek, Flow Laboratories, Inglewood, CA). The filters were dried, placed in scintillation vials containing 5 ml of 0.5% 2,5-diphenyloxazole and 0.04% p-bis-2-(5-phenyloxazole) benzene in toluene, and the incorporated [$^3$H] determined in a Packard TriCarb Liquid Scintillation Spectrometer. The stimulation index (SI) was calculated by dividing the CPM incorporated by lumphocytes cultured with each mitogen or antigen by the CPM incorporated by lymphocytes cultured with medium alone (in the case of the mitogens) or with uninfected control cells (in the case of the antigen-bearing infected cells).

Lymphocytes were prepared from rabbits and adult volunteers with and without prior HSV infection, as determined by clinical history and serum antibody testing. Lymphocytes were cultured alone, in the presence of mitogen (Con A or PHA), in the presence of uninactivated or inactivated HSV-infected cells, or in the presence of similarly treated uninfected control cells. Lymphocyte proliferation, as measured by [$^3$H]thymidine incorporation, was examined after six days of culture in vitro. A positive virus-specific response was defined as a stimulation index of greater than three. Lymphocytes from HSV immune donors demonstrated virus-specific stimulation whereas lymphocytes from nonimmune donors did not. At the same effector cell to target cell ratio, HSV-infected cells rendered noninfectious by psoralen-LWUV treatment stimulated immune lymphocytes to the same degree as did untreated HSV-infected cells (Table 5). On a per cell basis, it was also found that virus antigen dose-response curves were equivalent for psoralen-LWUV inactivated and uninactivated cells. Thus exposure to psoralen-LWUV treatment sufficient to totally abolish infectivity does not appear to alter the ability of virus antigen-bearing cells to stimulate the virus-specific proliferative response of immune lymphocytes.

TABLE 5

THE EFFECT OF PSORALEN LWUV INACTIVATION ON THE CAPACITY OF HSV-INFECTED CELLS TO STIMULATE IN VITRO VIRUS-SPECIFIC LYMPHOCYTE PROLIFERATION.

| | SOURCE OF LYMPHOCYTES | | | | | | | |
|---|---|---|---|---|---|---|---|---|
| | Nonimmune Rabbit | | Immune Rabbit | | Nonimmune Human | | Immune Human | |
| Mitogen or Antigen | CPM | SI | CPM | SI | CPM | SI | CPM | SI |
| Unifected cells ($2 \times 10^3$/culture) | 266 ± 11 | | 266 ± 75 | | 2724 ± 197 | | 708 ± 122 | |
| Uninactivated HSV-infected cells ($2 \times 10^3$/culture) | 303 ± 52 | 1.1 | 4758 ± 329 | 17.9 | 1544 ± 130 | 0.6 | 13,924 ± 1013 | 19.7 |
| Psoralen-LWUV inactivated HSV-infected cells ($2 \times 10^3$/culture) | 207 ± 10 | 0.8 | 4540 ± 266 | 17.0 | 3742 ± 507 | 1.4 | 15,457 ± 286 | 21.8 |
| None (Medium alone) | 459 ± 7 | | 264 ± 36 | | 1207 ± 303 | | 379 ± 51 | |
| Con A (50 ug/ml) | 46,676 ± 683 | 101.7 | 90,809 ± 12,161 | 344.0 | — | | — | |
| PHA (10 ug/ml) | — | | — | | 18,692 ± 1955 | 15.5 | 44,295 ± 1046 | 116.8 |

(b) Cytolysis of Virus-Infected Cells. HSV-infected cells are labelled with $^{51}$Cr as described by Bellanti, J. A., supra. Lymphocytes are prepared from rabbits and adult volunteers with and without prior HSV infection as described above. Lymphocytes are cultured alone, in the presence of uninactivated or inactivated HSV-infected cells or in the presence of similarly uninfected control cells as described by Bellanti, J. A., et al, supra. The cells and cell debris are removed by centrifugation and the amount of $^{51}$Cr in the supernatant is measured for each sample. A definite increase in the amount of $^{51}$Cr in the supernatant is observed when inactivated, virus-infected cells are cultured with immune lymphocytes. This increase is equivalent to that obtained for uninactivated, virus-infected cells cultured with immune lymphocytes. Thus, exposure to psoralen-LWUV treatment sufficient to totally abolish infectivity does not appear to alter the ability of virus antigen-bearing cells to stimulate the virus-specific cytotoxic response of immune lymphocytes.

EXAMPLE 6

Vaccine Containing Virus-Infected Cells

Since the inactivated, virus-infected cells are capable of eliciting a cellular immunity response, it therefore follows that the inactivated cells administered in a physiologically acceptable medium constitutes a vaccine for protection against the virus.

Sixteen chimpanzees are divided into four groups. Group A is inoculated intravenously with 1 ml of influenza virus. Group B is inoculated with 1 ml containing $10^6$ influenza virus-infected MDCK cells. Group C is inoculated with 1 ml containing $10^6$ inactivated, influenza virus-infected MDCK cells and Group D is the control group and received no inoculation. All chimpanzees in Groups A and B develop symptoms of influenza. None of the animals in Groups C and D develop symptoms of influenza. The chimpanzees of Group C are rendered immune to subsequent challenge when inoculated intraveneously with 1 ml of influenza virus or 1 ml containing $10^6$ influenza virus-infected MDCK cells.

While the invention has been described in connection with specific embodiments thereof, it will be understood that it is capable of further modifications. This application is intended to cover any variations, uses or adaptations of the invention following, in general, the principles of the invention and including such departures from the present disclosure as come within known and customary practice within the art to which the invention pertains.

What is claimed is:

1. A process for assaying cellular immunity which comprises (a) incubating lymphocytes with inactivated, non-infective virus-containing normal cells or tumor cells having cell associated antigens capable of eliciting an immunological response and having had DNA or RNA contained therein covalently bonded to psoralen or a psoralen derivative in the presence of long wave-length ultraviolet light, and (b) measuring the amount of lymphocyte proliferation.

2. The process of claim 1 wherein the virus is Herpes simplex virus.

3. The process of claim 1 wherein the virus is influenza virus.

4. The process of claim 2 wherein the cells are rabbit kidney cells.

5. The process of claim 3 wherein the cells are Madin Darby canine cells.

6. The process of claim 1 wherein step (a) is performed in the presence of a labelled deoxynucleotide.

7. The process of claim 6 wherein step (b) is performed by measuring the amount of incorporation of said labelled deoxynucleotide.

8. A process for assaying cellular immunity which comprises (a) incubating lymphocytes with labelled, inactivated, non-infective virus-containing normal cells or tumor cells having cell associated antigens capable of eliciting an immunological response and having had DNA or RNA contained therein covalently bonded to psoralen or a psoralen derivative in the presence of long wave-length ultraviolet light, and (b) measuring the amount of cytolysis of said cells.

9. The process of claim 8 wherein the virus is Herpes simplex virus.

10. The process of claim 8 wherein the virus is influenza virus.

11. The process of claim 9 wherein the cells are rabbit kidney cells.

12. The process of claim 10 wherein the cells are Madin Darby canine cells.

13. The process of claim 8 wherein said label is a radiolabel.

14. The process of claim 13 wherein step (b) is performed by measuring the amount of radiolabel released by the cytolysis of said cells.

* * * * *